United States Patent [19]

Koontz

[11] Patent Number: 4,610,710

[45] Date of Patent: Sep. 9, 1986

[54] METHOD FOR UTILIZING MAGNETIC FIELD SENSING MEANS FOR DETECTING DISCONTINUITIES IN A CONDUCTOR MEMBER ASSOCIATED WITH A GLASS SHEET

[75] Inventor: Harry S. Koontz, Pittsburgh, Pa.

[73] Assignee: PPG Industries, Inc., Pittsburgh, Pa.

[21] Appl. No.: 734,715

[22] Filed: May 16, 1985

Related U.S. Application Data

[62] Division of Ser. No. 491,683, May 5, 1983, Pat. No. 4,542,333.

[51] Int. Cl.$^4$ .................. C03C 27/02; G01R 33/00; G01R 31/08
[52] U.S. Cl. .................................. 65/29; 65/50; 65/59.1; 65/160; 324/52; 324/117 H
[58] Field of Search ............... 65/29, 50, 59.1, 160; 324/73 PC, 158 F, 117 H, 50, 52

[56] References Cited

U.S. PATENT DOCUMENTS

| | | | |
|---|---|---|---|
| 3,590,371 | 6/1971 | Shaw, Jr. | 324/51 |
| 4,362,991 | 12/1982 | Carbine | 324/158 F |
| 4,395,677 | 7/1983 | Petersdorf | 324/117 H |

Primary Examiner—Arthur Kellogg
Attorney, Agent, or Firm—Robert A. Westerlund, Jr.

[57] ABSTRACT

A method and apparatus for detecting discontinuities in electric conductor heating lines in automobile heated back lights is disclosed. The apparatus includes a "Hall effect" probe, a microprocessor, a display, a stepping motor drive, an optical scanner and associated circuitry. The method includes the steps of energizing the heating grid and moving a Hall effect probe in the vicinity of each conductor line. Any heater line having discontinuity will lack a detectable magnetic field.

10 Claims, 2 Drawing Figures

METHOD FOR UTILIZING MAGNETIC FIELD SENSING MEANS FOR DETECTING DISCONTINUITIES IN A CONDUCTOR MEMBER ASSOCIATED WITH A GLASS SHEET

This is a division of application Ser. No. 491,683, filed May 5, 1983 now U.S. Pat. No. 4,542,333.

BACKGROUND OF THE INVENTION

1. Field of the Invention

This invention relates to a method of detecting circuit discontinuities in conductor members supported by glass sheets, such as in a defrosting automobile back light.

2. Description of the Technical Difficulties

Windows for automobiles, and particularly back lights, used for automobiles are commonly provided with electric heating elements for defrosting and defogging. Such back lights are generally made from a Pattern cut flat glass sheet thermally bent or molded to fit the particular automobile window opening. Prior to the heating and bending of the glass sheet, a number of narrow spaced parallel lines of a conducting material is placed on the inside vision area of the glass. The parallel lines are connected on opposite adjacent margins thereof by a strip of electrodes of the same material which is generally a ceramic frit containing silver or silver oxide. Upon the heat of bending and tempering, the lines and strip electrode buses are fired onto the glass so that the pattern becomes part of the glass substrate. When the automobile electrical power source is connected to the strip electrode buses, the resultant resistant heating in the parallel strips defogs or defrosts the glass.

Normally the silver/silver oxide frit is applied by silk screening the pattern onto one surface of the glass sheet while it is still flat. During the subsequent treatment of the sheet by heating and bending the glass to the desired curvature, the frit material becomes tightly bonded to the glass surface.

Other glass sheets or substrates, such as aircraft transparencies have embedded in them a plurality of very fine conductor members, these being of copper or the like. The conductor members are of size, number, spacing and shape so as to not interfere with the transmission of light through the window and at the same time are such by the application of elecricity to suitable bus bars that it is possible to pass current through them and thereby heat the windshield for defogging or deicing.

Despite the manner in which the windshield or back light heating defrosting/defogging pattern is produced, it is likely that upon the manufacturing process, one or more breaks in the intended circuit pattern will occur. It is difficult to detect such breaks and is time consuming to view the piece of glass through a microscope so as to visually detect discontinuities.

One method of detecting the broken heater lines is described in U.S. Pat. No. 3,590,371 to Shaw. The Shaw patent teaches the use of detecting circuit discontinuities in glass sheets having conductor members embedded therein by placing in association with the glass a stratum of cholesteric-phase liquid-crystal material having appropriate color change temperature-range characteristics. The Shaw reference discloses passing current through the conductors and observing color changes in the vicinity of the operating conductors in the liquid crystal material. In practice, the Shaw invention includes a manual operation of placing a sheet of the temperature sensitive liquid crystal material over the inside surface of the horizontally positioned back light while power is applied to the heater grid. By observing the changing patterns in the liquid crystal material over a short period of time as the adjacent heater lines become hot by observing an ammeter in the power circuit the operator can tell which, if any, lines are broken and the amount of total current passing through the heater pattern. The operator after disconnecting the power and removing the liquid crystal sheets then records the observations manually.

Whereas the Shaw detection method produces good results in detecting discontinuities, due to the necessary manual operation it is not entirely suitable for an automatic detection system. Such an automatic detection system should be able to observe the broken or discontinuitous heater lines while the windshield or back light is passing through the manufacturing process. The detection system should not only record that a discontinuity has occurred but it should note the location and display the information so that the discontinuity can be repaired. It would be helpful if the method of detecting the discontinuity would not contact the glass, and would be capable of detecting the discontinuity as the glass part was moved underneath or would provide a movable probe over or under the heater lines so as to not produce marring or scratching. Further, it would be beneficial if such a testing inspection apparatus were provided that would be able to detect broken lines in silk screened pattern ceramic silver or silver oxide frit prior to being fused into the substrate as such a detecting means would enable the manufacturer to more conveniently repair discontinuitous lines prior to having those lines fused onto the glass substrate.

In 1879 E. H. Hall at John Hopkins University discovered that if a conductor while carring an electric field longitudinally was placed in a magnetic field with the conductor perpendicular to the direction of the field, that there was a difference of electric potential on either side of conductor. He also observed that if such points were joined through a sensitive galvanometer that a feeble current would be indicated. If such a Hall effect instrument is utilized in conjunction with a gaussmeter, the magnetic field surrounding a conducting material can be detected. The resulting device is known as a "Hall effect" probe.

SUMMARY OF THE INVENTION

The invention relates generally to a method and apparatus for detecting discontinuities in the conductor members in a defogging windshield or back light. The discontinuities in the conductor heated back light or similar substrate are detected by the use of a "Hall effect" magnetic field sensing probe which can detect the magnetic field associated with conducting member when the conducting member is conducting electricity. Accordingly, the invention provides a method of applying electric current to the conducting members and then scanning the heater lines with the "Hall effect" detection probe and observing the resultant magnetic field on each heater line. The lack of magnetic field associated with any heater line thus indicates a discontinuity. Not only can discontinuities be observed, but also anomolies wherein the width of a particular heater line is reduced or enlarged to the extent that it affects the magnetic field can be sensed by the "Hall effect" probe. In order to convert the magnetic field as sensed by the probe which produces a signal analagous to the magnetic field detected, it is necessary to condition the signal to convert the analog information into digital information. Accordingly, the invention includes the "Hall effect" sensing probe and an amplifier to amplify the analog signals so produced. Signal conditioning circuitry is provided to condition the analog signal and convert it to a digital signal to be processed by a microprocessor and then displayed. The display could be in the form of readily observable light emitting diodes (LEDs) which would be activated upon the presence and detection of a broken heater line. The display could also include a digital readout of the relative amplitude of the observed magnetic field and it could also include the amount of power applied to the heater pattern itself. The display could thus be a standard liquid crystal display or it could be a printed readout for producing labels which could then be placed on the glass and thus indicating the total "Hall effect" inspection.

In order to fully automate the method of detecting discontinuities, a glass edge sheet detection means is employed which then determines the distance from the glass edge to the first heater line in order to anticipate where magnetic field should be observed. Accurate clocking means and stepping motor is provided to determine the accurate positioning of the probe with respect to the heater lines. In order to keep the probe off the glass and the heater lines itself, the apparatus includes a wheel which suspends the probe from the glass and a bridge mechanism which can move the probe with respect to the glass while the glass is stationary and in a horizontal orientation. The wheel is only used to suspend the probe above the glass. It is also contemplated within the scope of the invention that upon the detection of a broken heater line that an alarm would be sounded when a discontinuity is observed so that that particular back light or windshield could be removed from the line for repair.

By the use of the instant invention a wide variety of heater line patterns could be manufactured in which the detection is automatic thus allowing for high volume production as well as also allowing batch production. The manual labor associated with prior art placing liquid crystal substrates over the glass is considerably reduced.

In order that the invention may be more clearly understood, there are the preferred embodiments of the invention which will now be described in reference to the accompanying drawings.

DESCRIPTION OF THE PREFERRED EMBODIMENT

Figure 1:
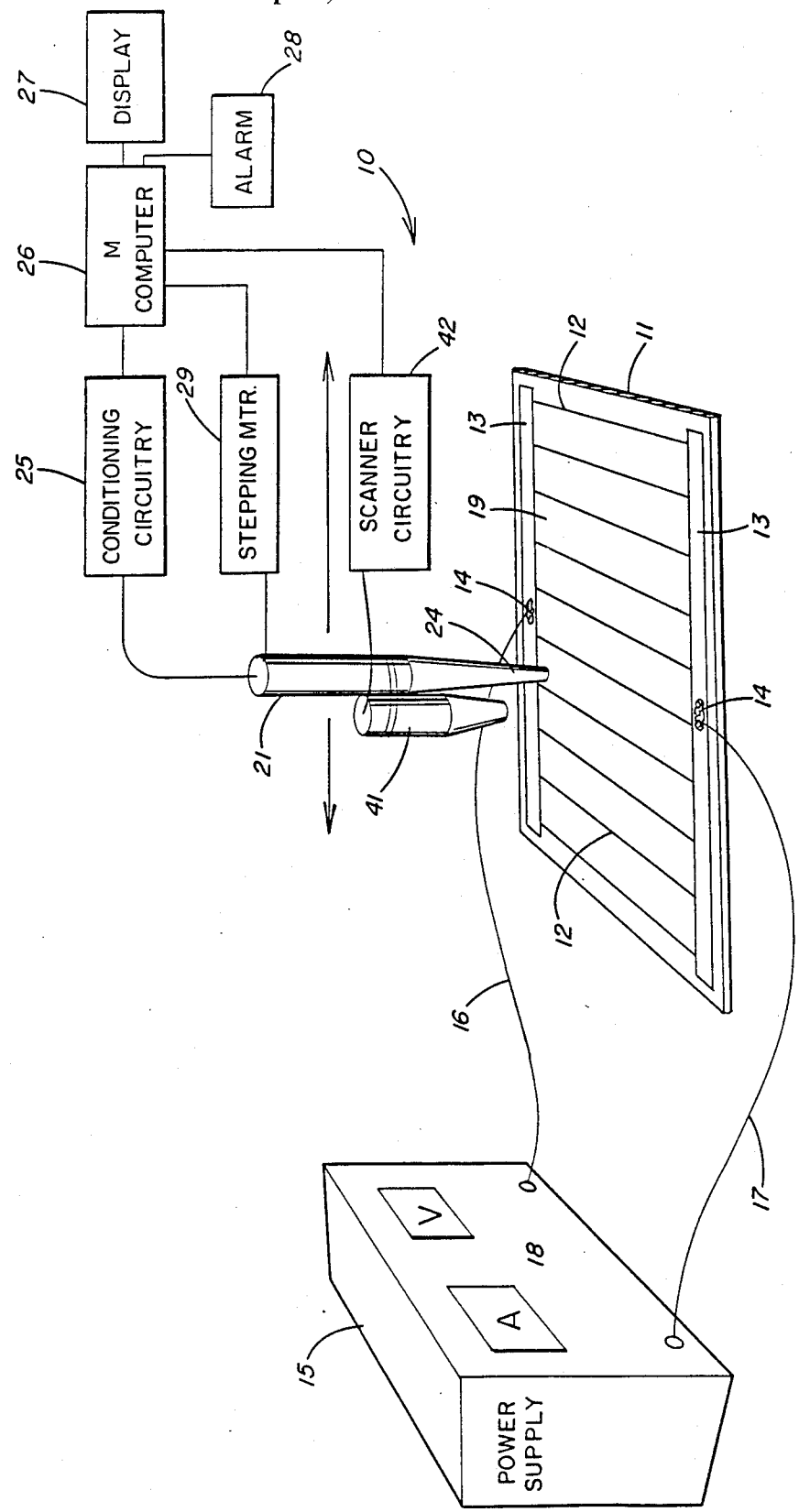
FIG. 1 is a diagrammatical depiction of the invention for detecting discontinuities in heater back light pattern lines showing a "Hall effect" probe utilized in conjunction with a heater back light grid on a sheet of glass in which the grid is connected to a power supply.

The apparatus 10 is shown generally in FIG. 1 in diagrammatic form in which a glass sheet 11 having heater lines 12 and bus bar 13 is connected at connection points 14 to power supply 15. The connection leads 16 and 17 complete a circuit between the power supply and the defogging heater lines 12. Ammeter 18 is placed between leads 16 and 17. The power supply provides a direct current which delivers a current as recorded by ammeter 18 appropriate for the particular pattern of heater lines 12 as defined by the automobile manufacturer who designed the heated back light 11. Heated back light 11 is a tempered glass sheet having ceramic silver or silver oxide frit pattern silk screened on the sheet 11 so as to produce bus bars 13 and heater lines 12 in an appropriate pattern. When the sheet 11 is heated to be bent and formed into the pattern, the silver or silver oxide frit is fused into the substrate of the glass. The instant invention can be utilized to detect broken heater lines prior to the time that the glass sheet 11 is tempered to thereby facilitate removal and repair of the heater lines, if any, which have been determined to be defective. However in the preferred embodiment the detection of broken heater lines is accomplished after the part has been bent, tempered and the pattern including bus bars 13 and lines 12 have been fused onto the glass sheet 11. The instant invention allows for detection of broken heater lines 13 without actually contacting the glass surface 19 and would work whether the heater lines 12 were placed on either side of the glass.

Figure 2:
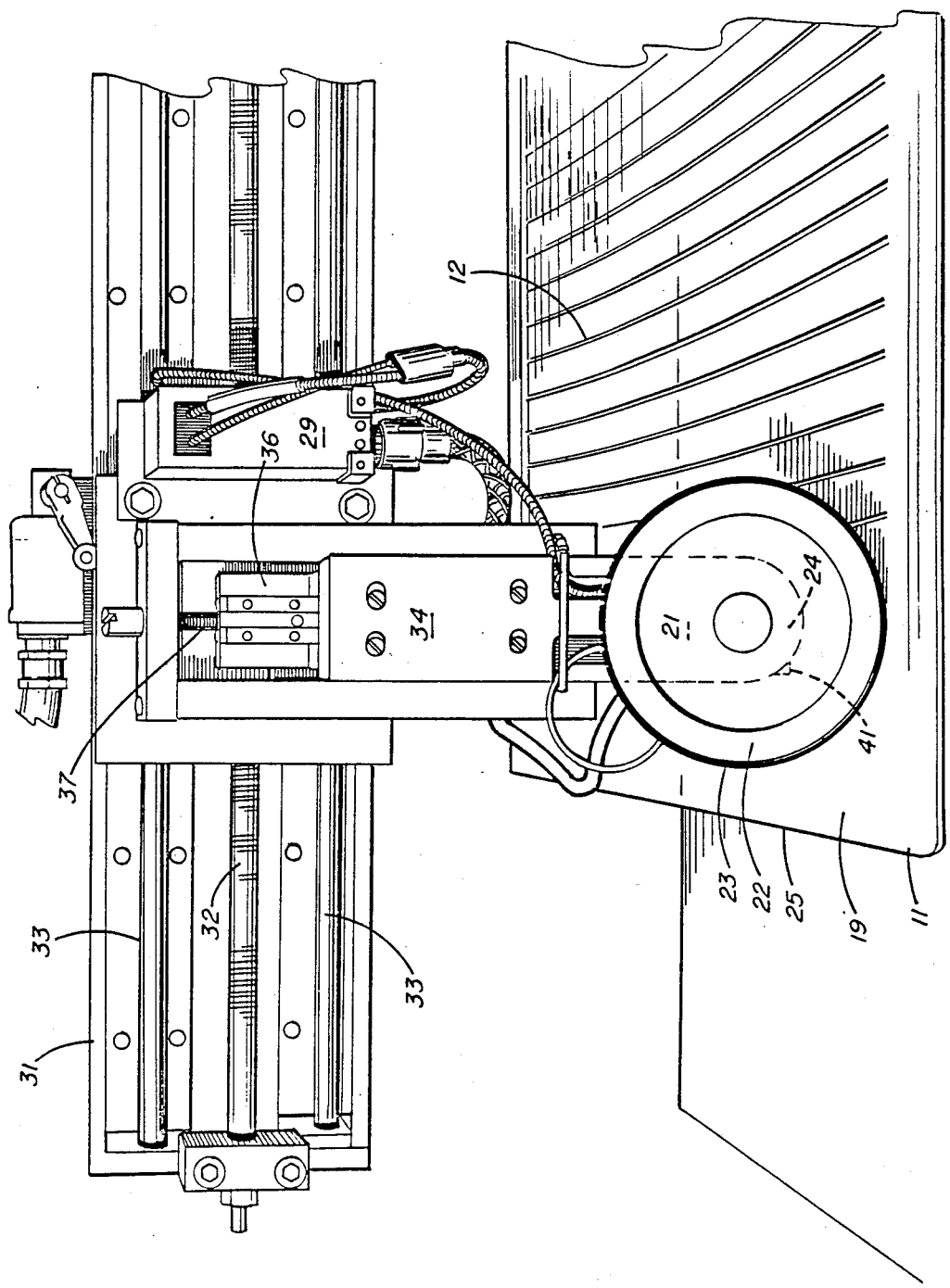
FIG. 2 is a right side perspective view of the sensing probe and movement mechanism to provide relative movement between the depicted glass sheet and the "Hall effect" probe.

In the preferred embodiment as depicted in FIG. 2, heater lines 12 are shown on the upper surface 19 of glass sheet 11 and the "Hall effect" probe 21 is suspended above glass surface 19 by use of suspension wheel 22. Suspension wheel 22 is provided with a rubber non-marring contacting surface 23. The purpose of having contact with glass surface 19 by wheel 22 is to maintain a constant distance above heater lines 12 as Hall effect probe 21 is moved across heater lines 12.

With reference to FIG. 1, it can be seen that "Hall effect" Probe 21 is provided with "Hall effect" probe tip 24 which is suspended above heater lines 12 in glass sheet 11. The "Hall effect" probe 21 is electrically connected to conditioning circuitry which includes circuits which will amplify the analog signals detected by "Hall effect" probe 21. The conditioning circuitry further includes electrical filters well known in the art as well as circuitry for producing a digital signal by squaring the analog signals produced by the "Hall effect" probe 21. "Hall effect" probe 21 is a probe which is commercially available from various suppliers. Conditioning circuitry 25 which produces a digital output signal such as the square wave is then operably connected to a microprocessor or computer which is capable of processing the digital signal to display the continuity information of the back light heater lines 12 as the "Hall effect" probe 21 is moved relative to glass sheet 11. Microprocessor 26 could be any commercial microprocessor, however it has been found that the Motorola 6800 Microprocessor provides acceptable results. The microprocessor 26 not only can provide a display of the magnetic field surrounding each heater back light as the "Hall effect" probe 21 passes over it also, it is capable of sounding an alarm 28 when the probe passes over a position where a magnetic field should be. In order to provide such an alarm information, it is necessary to know the glass movement distance with respect to the "Hall effect" probe 21 and have preprograamed the position of expected magnetic fields that relate to individual lines. Such a distance input to microprocessor 26 is provided by the use of a stepping motor 29 and associated circuitry.

It can be shown in FIG. 2 that stepping motor 29 will accurately measure relative travel between glass sheet 11 and Hall effect probe tip 24. In FIG. 2 it can also be seen in the preferred embodiment that a bridge 31 utilizing a screw shaft 32 and shafting 33 allows the "Hall effect" probe 21 to move in the direction of travel of relative motion between glass sheet 11 and "Hall effect" probe 21. Vertical movement is allowed by vertical slide 34 which is connected to compliancy slide 36. The pressure exerted against the glass by wheel 22 can be controlled by use of screw mechanism 37 which applies a biasing force to a spring in compliance to slide 36 thereby adjusting the amount of pressure against glass surface 12 so as not to mar the glass surface or to scratch heater lines 12 and to inspect curved glass.

In the preferred embodiment, the glass sheet 11 is held stationary and the "Hall effect" probe head is also provided with an optical scanner 41 which detects the edge 25 of glass sheet 11. The bridge 31 thus suspends the optical scanner 41 as well as "Hall effect" probe 21 having "Hall effect" probe tip 24 above the back light 11 being checked. As the steppig motor drives the "Hall effect" probe 21 along and above the back light heater lines, the optical sensor 41 signals microprocessor 26 when the optical scanner 41 is over the glass surface 19 and the Hall Effect probe 21 which is also non-contacting signals microprocessor 26 each time that probe tip 24 has passed through a magnetic field created by an electric current passing through a heater line 12. During this time pulses driving the stepping motor 29 are sent to the microprocessor 26 which thus provides a movement distance clock to signal the program logic in microprocessor 26. The signals received from optical scanner 41 are processed through conditioning scanning circuitry 42 prior to being inputted into microprocessor 26.

It has been found that if the instant invention 10 is placed on a conveyor or other automatic movement mechanisms, that additional inputs into the microprocessor 26 such as "initial set up", "run automatic", and "stop alarm" are also beneficial in that by use of such inputs and logic in the program for the microprocessor 26 that the microprocessor 26 can therefore control the movement of the motor both forward and reverse direction as well as to adquately provide for displays representing that the inspection is complete as well as producing an alarm or LED or other display representing a heater line 12 having a discontinuity.

It is perceived that the instant invention 10 could be placed upon an industrial robot (not shown) which would thereby move optical scanner 41 and "Hall effect" probe 21 over the surface of the glass 19 including heater lines 12 to detect any discontinuities. The invention contemplates relative movement between "Hall effect" probe 21 and heater lines 12. The relative movement could be provided by moving the probe 21 or by moving the heater lines 12 or by movement of both.

As can be appreciated from the foregoing description of the preferred embodiment, the invention is not limited to the above example which is presented for illustration purposes only. It is understood that other steps, examples, components, and methods of operation would occur to those skilled in the art from a thorough reading of this disclosure without departing from the scope of the invention as claimed hereinafter.

I claim:

1. In a method for fabricating an electrically heatable glass sheet including the steps of applying a heater grid comprised of electroconductive paste material to a surface of the glass sheet, and thereafter heating the paste material to fuse the heater grid to the glass surface, the improvement comprising the step of employing a magnetic field sensing means, prior to the heating step, to determine which, if any, of the heater lines of the grid are defective prior to the paste material being fused to the glass surface, to facilitate removal and repair of the heater lines, if any, which have been determined to be defective.

2. The improvement as set forth in claim 1, wherein said magnetic field sensing means comprises a "Hall Effect" sensor.

3. The improvement as set forth in claim 2, wherein said employing step comprises the sub-steps of:
    applying electric current to the heater lines;
    moving the glass sheet and said "Hall Effect" sensor relative to one another;
    wherein said sensor detects the magnetic field associated with each of the heater lines; and
    providing information about the magnetic field associated with each of the heater lines in response to said sensor detecting step, wherein the absence of a detectable magnetic field associated with any particular heater line(s) indicates electrical discontinuity or other deficiency of said any particular heater line(s).

4. The improvement as set forth in claim 3, wherein said sensor is disposed nearer to said glass sheet surface on which the heater grid is disposed than to the opposite glass sheet surface.

5. The improvement as set forth in claim 3, wherein said sensor and the glass sheet are maintained in spaced relation to each other during said employing step by means of a rollable wheel having a non-marring circumferential periphery in rolling contact with the glass surface.

6. The improvement as set forth in claim 5, wherein said moving sub-step comprises maintaining said sensor in a fixed position and moving the glass sheet therepast on an automotive lite fabrication conveyor line.

7. The improvement as set forth in claim 5, wherein said moving sub-step comprises maintaining said glass sheet in a fixed position and moving said sensor thereacross.

8. The improvement as set forth in claim 5, wherein said rollable wheel is vertically adjustable to vary the contact pressure of said rollable wheel periphery with the glass surface.

9. The improvement as set forth in claim 8, wherein the glass sheet is an automotive lite.

10. The improvement as set forth in claim 5, wherein said moving sub-step comprises moving both said glass sheet and said sensor.

* * * * *